United States Patent [19]

Koizumi

[11] Patent Number: 4,743,111
[45] Date of Patent: May 10, 1988

[54] EMISSION SPECTROCHEMICAL ANALYZER

[75] Inventor: Hideaki Koizumi, Katsuta, Japan

[73] Assignee: Hitachi, Ltd., Tokyo, Japan

[21] Appl. No.: 648,261

[22] Filed: Sep. 7, 1984

[30] Foreign Application Priority Data

Sep. 9, 1983 [JP] Japan ............................ 58-165198

[51] Int. Cl.⁴ .......................................... G01N 21/73
[52] U.S. Cl. .................................................. 356/316
[58] Field of Search ............... 356/307, 311, 312, 315, 356/316, 51

[56] References Cited

U.S. PATENT DOCUMENTS 3,449,565  6/1969  Barringer ........................ 356/351
4,035,083  7/1977  Woodriff et al. .................. 356/307
4,068,125  1/1978  Bell .................................. 250/343

Primary Examiner—F. L. Evans
Attorney, Agent, or Firm—Antonelli, Terry & Wands

[57] ABSTRACT

An improved emission spectrochemical analyzer is disclosed in which light from a sample in high-temperature plasma is led to an absorption cell, a magnetic field is applied to the absorption cell to utilize the Zeeman effect, the absorption cell is further pressurized to make the width of the absorption line of a desired element equal to the width of the resonance emission line of the element, and only the resonance emission line of the element is selected by appropriate modulation means and detected at high sensitivity.

8 Claims, 6 Drawing Sheets

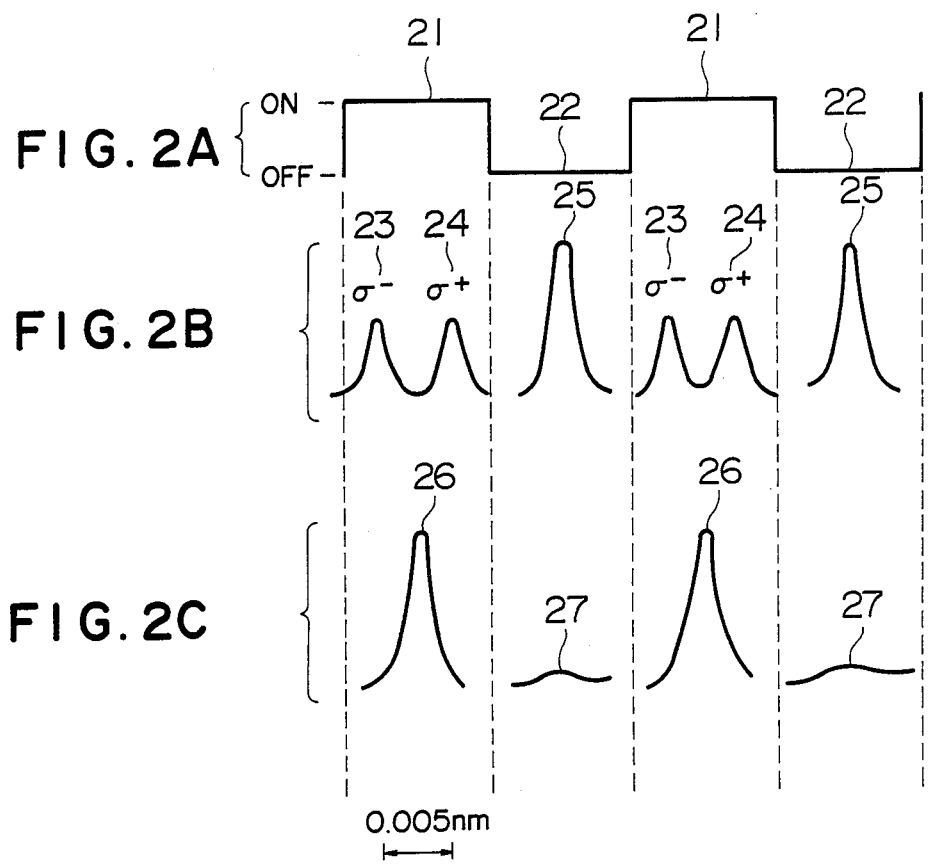

EMISSION SPECTROCHEMICAL ANALYZER

BACKGROUND OF THE INVENTION

The present invention relates to an emission spectrochemical analyzer used for the determination of a trace element.

Arc discharge, d.c. plasma, a Grimm lamp, microwave plasma, and others have hitherto been used as a light source for emission spectrochemical analysis. Recently, inductively coupled plasma (hereinafter referred to as "ICP") has been widely used as such a light source. Since these light sources have an exciting temperature of several thousands to ten thousand degree, they emit not only the atomic spectral lines of a desired element, but also an infinite number of atomic spectral lines of other elements and an intense, continuous spectrum. The spectral lines of other elements and the continuous spectrum interfere with the measurement of the spectral lines of the desired element. In order to remove the undesirable spectral lines and continuous spectrum, a conventional emission spectrochemical analyzer is required to include a large-sized spectroscope having a high resolving power.

SUMMARY OF THE INVENTION

An object of the present invention is to provide an emission spectrochemical analyzer which is high in sensitivity and excellent in selectivity without using a large-sized spectroscope having a high resolving power. In order to attain the above object, according to the present invention, there is provided an emission spectrochemical analyzer in which an atomic absorption line of an element to be detected is modulated with respect to wavelength or direction of plane of polarization on the basis of the Zeeman effect, to detect a signal based upon an emission line of the element.

BRIEF DESCRIPTION OF THE DRAWINGS

FIGS. 2A to 2C are graphs for explaining the operation principle of the embodiment shown in FIG. 1.

DESCRIPTION OF THE PREFERRED EMBODIMENT

A novel method of removing the undesirable spectral lines and continuous spectrum is carried out in an embodiment of an emission spectrochemical analyzer according to the present invention. That is, light emitted from ICP or the like passes through a previously-prepared atomic vapor for modulation, to modulate only the resonance emission line of a desired element, and a continuous spectrum and spectral lines other than the resonance emission line are removed by taking out only the resonance emission line. The Zeeman effect is used for modulating an atomic absorption line. In more detail, the atomic vapor for modulation is applied with a magnetic field, to slightly shift the wavelength of the atomic absorption line or to show a polarization characteristic in the absorption of the resonance emission line by the atomic vapor. Further, an absorption cell is pressurized so that the absorption line matches the emission line in line width. Especially, in the case where high-temperature plasma is used as a light source, the absorption cell is pressurized to enlarge the width of the absorption line. Furthermore, the strength of the magnetic field and the pressure inside the pressurized absorption cell are set to optimum values, to make sufficient modulation for the emission line from the practical point of view.

Figure 1:
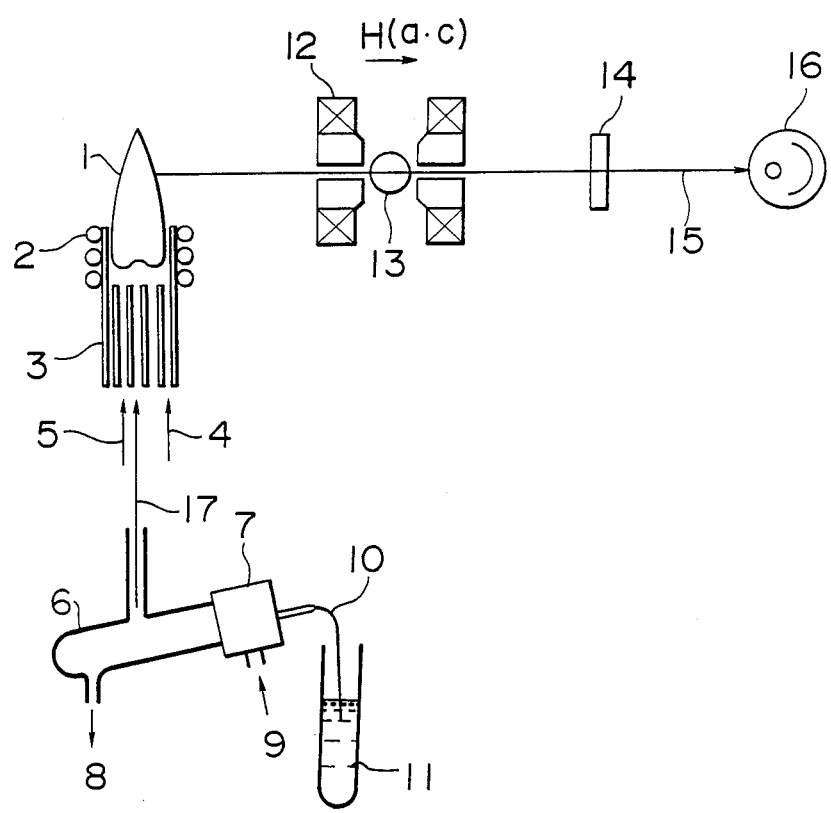
FIG. 1 is a schematic view showing the outline of an embodiment of an emission spectrochemical analyzer according to the present invention.

FIG. 1 shows the outline of an embodiment of an emission spectrochemical analyzer according to the present invention. The light emitting part of the present embodiment is formed of an ICP device, by way of example. Referring to FIG. 1, a high-frequency induction coil 2 is disposed around a quartz tube 3 having a diameter of about 15 mm to supply a plasma flame 1 with a high-frequency power of 1 to 3 KW (having a frequency of 27.12 MHz). The quartz tube 3 has a three-cylinder structure, and therefore two cylindrical spaces and a central space are formed in the quartz tube 3. A plasma gas 4 flows through the outer one of the cylindrical spaces at a flow rate of 15 to 20 l/min, an auxiliary gas 5 flows through the inner cylindrical space at a flow rate of 0.5 to 2 l/min, and a nebulizer gas 9 containing a sample flows through the central space, in the form of a sample mist 17, at a flow rate of 0.3 to 0.5 l/min. In general, argon is used as the plasma gas, auxiliary gas, and nebulizer gas. An aqueous solution 11 is used as the sample, and is sucked into a nebulizer 7 through a capillary tube 10. The sample thus sucked is sent through a chamber 6 having a drain 8 to a central portion of the plasma flame 1 in the form of mist. The plasma flame 1 has a temperature of 7,000° to 9,000° K., and emits the continuous spectrum of argon and a large number of spectral lines of coexisting elements, in addition to spectral lines of a desired element (namely, an element to be detected). In the present embodiment, in order to select only the analytical line of the desired element from the above-mentioned continuous spectrum and spectral lines and to detect the analytical line at high sensitivity, an atomic absorption cell 13 containing the desired element is interposed between the pole pieces of an a.c. electromagnet 12, and light 15 from the plasma flame 1 is forced to pass through the cell 13 in a direction parallel to a magnetic field H applied to the cell 13. An optical filter 14 is disposed in front of a photomultiplier 16 which is a photoelectric converter for the light 15.

FIGS. 2A to 2C show the relationship between the magnetic field H shown in FIG. 1 and the emission and absorption lines at the cell 13. It is to be noted that the absorption line has a width due to the pressure effect which will be explained later. FIG. 2A shows the state of the magnetic field H, FIG. 2B the state of the absorption line, and FIG. 2C the state of the resonance emission line. In FIG. 2A, reference numeral 21 designates a period when the magnetic field is applied to the cell 13, and 22 a period when the magnetic field is not applied. Further, in FIG. 2A, the abscissa indicates time. In FIG. 2B, reference numeral 23 designates a $\sigma^-$-component due to the Zeeman splitting based upon the magnetic field H, 24 a $\sigma^+$-component due to the Zeeman splitting, and 25 the unsplit, original absorption line. Further, in FIG. 2B, the abscissa indicates a wavelength. In FIG. 2C, reference numeral 26 designates the emission line having passed through the cell 13 at the period when the magnetic field is applied to the cell 13, and 27 the emission line having passed through the cell 13 at the period when the magnetic field is not applied. Further, in FIG. 2C, the abscissa indicates a wavelength.

In a state that the magnetic field is applied to the cell 13, the absorption line splits into the $\sigma^+$-component and $\sigma^-$-component, as shown in FIG. 2B. When the magnetic field is removed, the absorption line returns to an unsplit, original state. Of light components emitted from the plasma, only the resonance emission line of the desired element is absorbed by the atomic absorption cell 13 at the period when the magnetic field is not applied. When the magnetic field is applied to the cell 13, the absorption line splits into the two components, and thus the resonance emission line is not absorbed by the cell 13. These states are shown in FIG. 2C. As mentioned above, of the light components emitted from the plasma, only the resonance emission line is intensity-modulated by the magnetic field. The remaining light components are not modulated by the magnetic field. Accordingly, by carrying out lock-in amplification for a signal indicative of the resonance emission line, at the same frequency as the frequency of the a.c. magnetic field, only the resonance emission line of the desired element can be selected. The a.c. electromagnet, which acts as a reactive load, is a laminate-type magnet, and is connected to an appropriate capacitor so that a resonant state is obtained at a frequency of 50 or 60 Hz. Electric power for the electromagnet is supplied from an indoor wire for the lightlamp to the electromagnet through a stabilizer. The half-width of an emission line produced in the plasma having a temperature of about 8,000° K. depends mainly upon the Doppler width. It can be known by calculation that the Doppler width of the resonance line of cadmium having a wavelength of 228.8 nm is about 10 GHz (corresponding to a wave number of 0.33 cm$^{-1}$) The Doppler width $\Delta\nu_D$ is calculated from the following equation:

$$\Delta\nu_D = \frac{2\sqrt{2R \ln 2}}{c} \cdot \nu_o \sqrt{\frac{T}{M}} \quad (1)$$

where c indicates the light velocity, R the gas constant, $\nu_o$ the oscillation frequency of an atomic spectral line, T an absolute temperature, and M the mass of an atom. As can be seen from the equation (1), the Doppler width (namely, Doppler broadening) $\Delta\nu_D$ increases as the mass M is smaller. For example, the Doppler broadening of the resonance line of lithium is 18 GHz at 8,000° K.

The atomic absorption cell used in the present embodiment is pressurized, as will be explained below. Since the temperature of the atomic absorption cell is far lower than that of the plasma, the Doppler broadening of absorption line at the cell is small. Accordingly, if the atomic absorption cell is left as it is, the resonance emission line from the plasma will not be sufficiently absorbed by the cell, as indicated, in FIG. 3B, by an emission line 33 having passed through the cell 13. Therefore, the atomic absorption cell is pressurized, to utilize the Lorentz effect (namely, pressure effect) instead of the Doppler effect. The Lorentz broadening $\Delta\nu_L$ is expressed by the following equation:

$$\Delta\nu_L = 1.95 \times 10^{19} p \, \sigma_L^2 \sqrt{\frac{2R}{\pi T}\left(\frac{1}{M} + \frac{1}{M_o}\right)} \quad (2)$$

where p indicates a pressure, $\sigma_L^2$ the effective sectional area of the Lorentz effect, and $M_o$ the atomic weight of a coexisting gas.

Figure 3A:
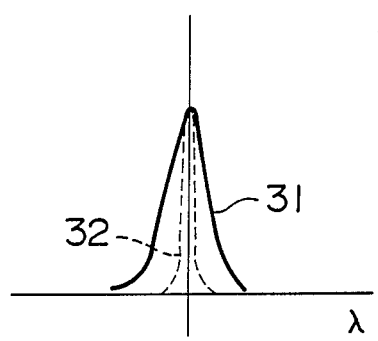
FIGS. 3A and 3B are graphs for explaining the atomic absorption of light according to a conventional method.
Figure 3B:
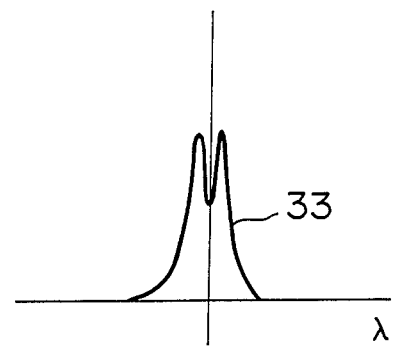
Figure 4A:
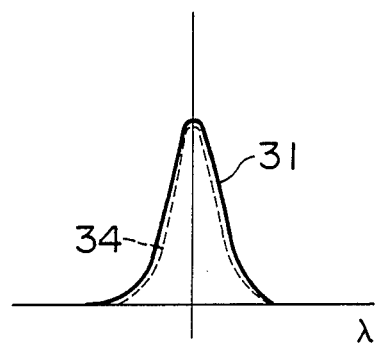
FIGS. 4A and 4B are graphs for explaining the atomic absorption of light according to the present invention.
Figure 4B:
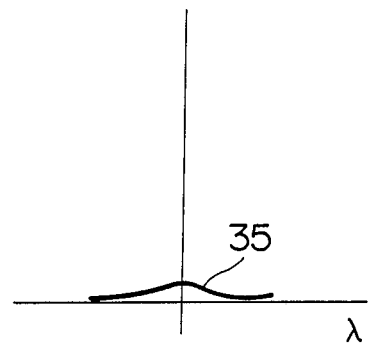

FIGS. 3A and 3B show the case where the atomic absorption cell is not pressurized, and FIGS. 4A and 4B show the case where the cell is pressurized. In FIGS. 3A, 3B, 4A, and 4B, reference numeral 31 designates an emission line, 32 an atomic absorption line, 33 the emission line having passed through the atomic absorption cell at the period when the magnetic field is not applied, 34 the atomic absorption line at the pressurized cell, and 35 the emission line having passed through the pressurized cell at the period when the magnetic field is not applied. When argon is introduced, as the coexisting gas, into the atomic absorption cell to a pressure of several atm., the width of the absorption line increases and becomes nearly equal to the width of the emission line from the plasma having a temperature of 8,000° K. FIG. 4B shows that the emission line is sufficiently absorbed by such a pressurized cell. The detailed structure of the pressurized atomic absorption cell is shown in FIG. 5.

Figure 5:
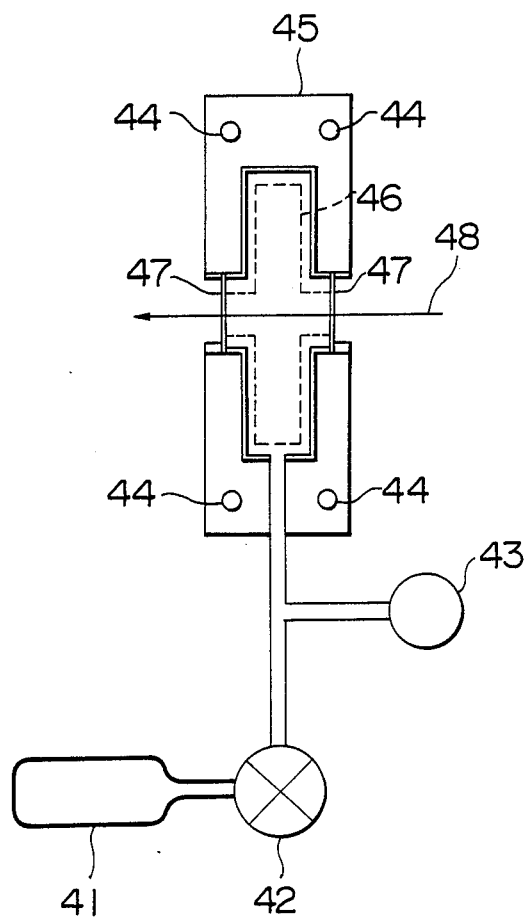
FIG. 5 is a schematic view showing the structure of a pressurized atomic absorption cell.

In FIG. 5, reference numeral 41 designates a high-pressure gas cylinder, 42 a pressure adjusting valve, 43 a pressure gauge, 44 a plurality of heaters, 45 a heat block, 46 a heat-resisting net, 47 a light transmitting window, and 48 a light beam. The atomic absorption cell shown in FIG. 5 includes a heat pipe. One of elements such as sodium, lithium, cadmium, and zinc is charged in the cell, and then the cell is heated by the heaters 44 so that the charged element has a vapor pressure of 10$^{-1}$ Torr. Simultaneously, argon is introduced from the gas cylinder 41 into the cell to a pressure of several atm., to pressurize the cell. The pressure of argon is determined depending upon the charged element, and is adjusted so as to make the modulation for a detection signal as large as possible.

Further, it is desirable to adjust the intensity of the magnetic field applied to the cell so that the Zeeman shift is nearly equal to the width of the emission line produced in the plasma.

For example, the resonance emission line of cadmium produced in the plasma having a temperature of 8,000° K. has a width of 10 GHz, and the Zeeman shift of the absorption line of cadmium can be made equal to 10 GHz by applying a magnetic field of 7 KG to the absorption cell.

In general, a resonance emission line from the plasma can be sufficiently intensity-modulated by applying an a.c. magnetic field of 5 to 10 KG to the atomic absorption cell.

Light other than the resonance emission line of a desired element can be removed in the above-mentioned manner. However, of fluctuating components (namely, noise components) of the removed light, a component having a frequency nearly equal to the modulation frequency is mixed into a detection signal. Thus, the S/N ratio of the detection signal is reduced. In the present embodiment, such an undesirable light component is removed by the optical filter 14 shown in FIG. 1, or a spectroscope, and thus a high S/N ratio is obtained.

Figure 6A:
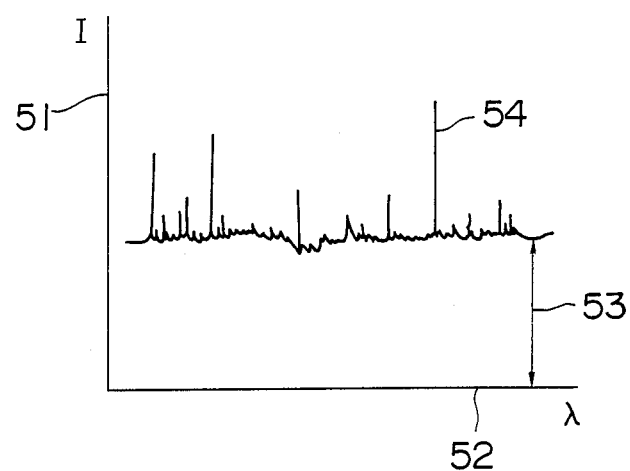
FIG. 6A is a graph showing an observational result obtained by a conventional method.
Figure 6B:
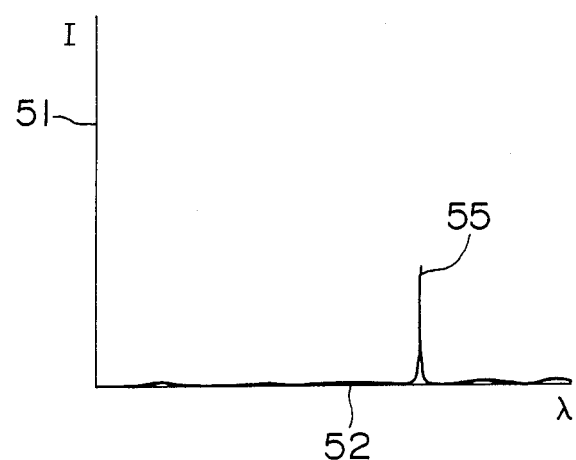
FIG. 6B is a graph showing an observational result according to the present invention.

FIGS. 6A and 6B show light detected by a conventional method and light detected by the above-mentioned method, respectively. In FIGS. 6A and 6B, the abscissa 52 indicates a wavelength, and the ordinate 51 a measured light intensity. In FIG. 6A showing the light detected by the conventional method, the resonance emission line 54 of a desired element is placed on a continuous spectrum 53. While, FIG. 6B shows that, according to the present invention, only the resonance emission line 55 of the desired element is observed. In more detail, FIGS. 6A and 6B show the results obtained when an emission spectrum from an ICP device is observed by a medium-sized spectroscope having a resolving power of 0.2 nm. As shown in FIG. 6A, the intensity of the continuous spectrum 53 is comparable to the intensity of emission lines of each of various elements contained in samples at a concentration of 1 to 100 ppm. Specifically, in the case where iron is contained in a sample, a vast number of emission lines are observed. However, in FIG. 6B, the complicated spectrum is removed, and only the resonance emission line of a desired element is observed.

The present embodiment is small in size, simple in structure, and high in sensitivity. Moreover, it can eliminate an interfering spectrum.

Figure 7A:
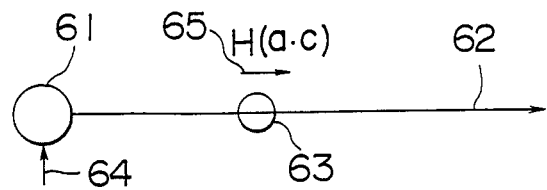
FIGS. 7A to 7C are schematic views showing various arrangements for modulating an emission line of a desired element on the basis of the Zeeman effect.
Figure 7B:
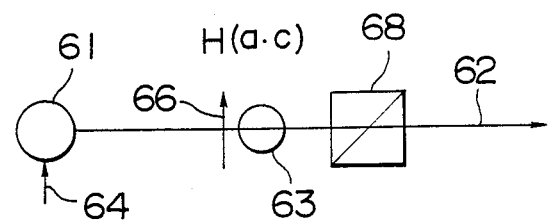
Figure 7C:
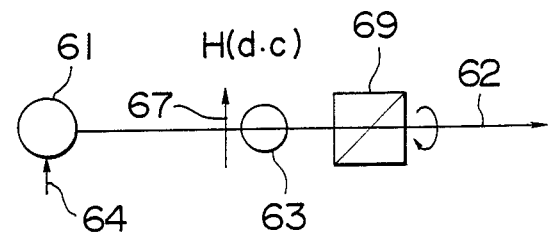

The intensity of a resonance line can be modulated on the basis of the Zeeman effect in various manners, as shown in FIGS. 7A to 7C. FIG. 7A shows the case where the Zeeman longitudinal effect is utilized as in the above embodiment, and FIGS. 7B and 7C show the case where the Zeeman transversal effect is utilized. In FIGS. 7A to 7C, reference numeral 61 designates a plasma light source, 62 a light beam, 63 an atomic absorption cell, 64 a sample introduced into the light source, 65 an a.c. magnetic field parallel to the light beam, 66 an a.c. magnetic field perpendicular to the light beam, 67 a d.c. magnetic field perpendicular to the light beam, 68 a fixed polarizer, and 69 a rotating polarizer.

As has been explained in the foregoing, according to the present invention, emission spectrochemical analysis can be made at high sensitivity, without using a large-sized spectroscope having a high resolving power.

I claim:

1. An emission spectrochemical analyzer including a light emitting part where a sample is introduced into inductively coupled plasma for emitting an atomic emission line therefrom, an atomic absorption part in which a desired element is introduced and is disposed on the path of the atomic emission line from the light emitting part and applied with a magnetic field, and a measuring part for measuring the intensity of the atomic emission line having passed through the atomic absorption part, wherein the pressure of the inner atmosphere of the atomic absorption part is increased to enlarge the width of an atomic absorption line of the desired element.

2. An emission spectrochemical analyzer according to claim 1, wherein the atomic absorption line at the atomic absorption part matches the atomic emission line in line width.

3. An emission spectochemical analyzer according to claim 1, wherein the pressure of the inner atmosphere of the atomic absorption part is adjusted so that the width of the atomic absorption line at the atomic absorption part is substantially equal to the width of the atomic emission line.

4. An emission spectrochemical analyzer according to claim 1, wherein the light emitting part emits a broad atomic emission line, the atomic absorption part without an increase of the pressure of the inner atmosphere thereof providing an atomic absorption line of the desired element having a width which is substantially narrower than the width of the atomic emission line, the pressure of the inner atmosphere of the atomic absorption part being increased to enlarge the width of the atomic absorption line of the desired element so as to substantially match the atomic emission line emitted by the light emitting part in line width thereby enabling an increase in detection sensitivity.

5. An emission spectrochemical analyzer comprising light emitting means where a sample is introduced into inductively coupled plasma for emitting an atomic emission line therefrom, atomic absorption means in which a desired element is introduced and which is disposed on the path of the atomic emission line from the light emitting means and applied with a magnetic field, and measuring means for measuring the intensity of the atomic emission line having passed through the atomic absorption means, the atomic absorption means being provided with an inner pressure which is increased to a value sufficient to enlarge the width of an atomic absorption line of the desired element to thereby absorb the atomic emission line.

6. An emission spectrochemical analyzer according to claim 5, wherein the atomic absorption means is provided with a pressure having a value so as to enable the atomic absorption line at the atomic absorption means to match the atomic emission line in line width.

7. An emission spectrochemical analyzer according to claim 5, wherein the atomic absorption means is provided with a pressure having a value sufficient to enable the width of the atomic absorption line at the atomic absorption means to be substantially equal to the width of the atomic emission line.

8. An emission spectrochemical analyzer according to claim 5, wherein the light emitting means emits a broad atomic emission line, the atomic absorption means without an increase of the pressure of the inner atmosphere thereof providing an atomic absorption line of the desired element having a width which is substantially narrower than the width of the atomic emission line, the pressure of the inner atmosphere of the atomic absorption means being increased to enlarge the width of the atomic absorption line of the desired element so as to substantially match the atomic emission line emitted by the light emitting means in line width thereby enabling an increase in detection sensitivity.

* * * * *